United States Patent
Jung et al.

(10) Patent No.: US 10,241,065 B2
(45) Date of Patent: Mar. 26, 2019

(54) ANALYSIS METHOD FOR POLYOLEFIN BRANCHES AND SYSTEM USING SAME

(71) Applicant: LG CHEM, LTD., Seoul (KR)

(72) Inventors: Minhwan Jung, Daejeon (KR); Hyesung Cho, Daejeon (KR); Yura Lee, Daejeon (KR); Sooyoung Kwak, Daejeon (KR)

(73) Assignee: LG CHEM, LTD., Seoul (KR)

( * ) Notice: Subject to any disclaimer, the term of this patent is extended or adjusted under 35 U.S.C. 154(b) by 442 days.

(21) Appl. No.: 14/910,585

(22) PCT Filed: Oct. 16, 2014

(86) PCT No.: PCT/KR2014/009756
§ 371 (c)(1),
(2) Date: Feb. 5, 2016

(87) PCT Pub. No.: WO2015/057002
PCT Pub. Date: Apr. 23, 2015

(65) Prior Publication Data
US 2016/0178547 A1    Jun. 23, 2016

(30) Foreign Application Priority Data

Oct. 18, 2013    (KR) .................. 10-2013-0124625

(51) Int. Cl.
*G01N 24/08*    (2006.01)
*G01N 33/44*    (2006.01)
*G01R 33/46*    (2006.01)

(52) U.S. Cl.
CPC ........... *G01N 24/087* (2013.01); *G01N 33/44* (2013.01); *G01R 33/4625* (2013.01); *G01R 33/4633* (2013.01)

(58) Field of Classification Search
CPC .. G01N 24/078; G01N 33/44; G01R 33/4625; G01R 33/4633
USPC ....................................................... 436/173
See application file for complete search history.

(56) References Cited

FOREIGN PATENT DOCUMENTS

| | | |
|---|---|---|
| JP | 55-012114 A | 1/1980 |
| JP | 2003194750 A | 7/2003 |
| JP | 2006-058271 A | 3/2006 |
| KR | 10-2007-0088724 A | 8/2007 |
| KR | 10-2011-0015252 A | 2/2011 |

OTHER PUBLICATIONS

J. Randall, "Carbon-13 NMR of Ethylene-1-Olefin Copolymers: Extension to the Short-Chain Branch Distribution in a Low-Density Polyethylene" (J. Polym. Sci—Polym. Phys. Ed., vol. 11, 275-287, (1973) (Year: 1973).*
Locatelli et al., "C13 NMR Analysis of Propene-Butene Copolymer. Steric Structure of Chain End Groups and Inhomogeneity of Isotactic Sites" (Macromolecules 1990, 23, 2406-2409). (Year: 1990).*
Dai, Yi, "1H Detection Heteronuclear Two-dimensional NMR Experiment," Foreign Analytical Instrumentation, 1998 (2), and English translation, 20 pages.
James C. Randall, "Carbon-13 NMR of ethylene-1-olefin copolymers: Extension to the short-chain branch distribution in a low-density polyethylene," Journal of Polymer Science: Polymer Physics Edition, 1973, vol. 11, pp. 275-287.
Klimke et al., "Optimisation and Application of Polyolefin Branch Quantification by Melt-State 13C NMR Spectroscopy," Macromolecular Chemistry and Physics, 2006, vol. 207, pp. 382-395.
Liu et al., "Poly(ethylene-co-1-octene) Characterization by High-Temperature Multidimensional NMR at 750 MHz," American Chemical Society, 2001, vol. 34, pp. 4757-4767.
Hansen et al., "Quantitative Determination of Comonomer Content in Ethene- -Alkene Copolymers by Solid State 1H-MAS NMR (Ethene--Hexene)," International Journal of Research and Reviews in Applied Sciences, 2011, vol. 6(4), pp. 382-390.
Yongae Kim, "Introduction of Solid NMR Spectroscopy and Application to Characterization for Polymeric Material," Polymer Science and Technology, 2011, vol. 22(1), pp. 50-56.
Search Report of European Patent Office in Appl'n No. 14853942.2, dated Nov. 30, 2016.
Office Action of Japanese Patent Office in Appl'n No. 2016-531562, dated Jan. 10, 2017.
Subramanyam, et al.: "A study of the structure of poly(hexene-1) prepared by nickel(alfa-diimine)/MAO catalyst using high resolution NMR spectroscopy", XP004508691, Polymer, Elsevier Science Publishers B.V, vol. 45, No. 12, May 1, 2004, pp. 4063-4076.
Subramanyam, U et al, "A study of the structure of poly(hexene-I) prepared by nickel (@a-diimine)/MA0 catalyst using high resolution NMR spectroscopy," vol. 45, No. 12, 2004, pp. 4063-4076.
McCord, E.F. et al, "Short-Chain Branching Structures in Ethylene Copolymers Prepared by High-Pressure Free-Radical Polymerization: An NMR Analysis," Macromolecules, vol. 30, No. 2, 1997, pp. 246-256.
Minhwan, Jung et al, "Analysis of Chain Branch o f Polyolefins by a New Proton NMR Approach," Analytical Chemistry, vol. 88, No. 3, 2016, pp. 1516-1520.

\* cited by examiner

*Primary Examiner* — Ling Siu Choi
*Assistant Examiner* — Ronald Grinsted
(74) *Attorney, Agent, or Firm* — Dentons US LLP

(57) ABSTRACT

This invention relates to a method of analyzing polyolefin branches and a system using the same, the method including: a) obtaining a spectrum for a sample including polyolefin having a plurality of branches using a nuclear magnetic resonance (NMR) spectrometer and a pulse program, wherein peaks of the branches are separated from each other in the spectrum; and b) calculating the proportion of each of the branches using the separated peaks.

12 Claims, 6 Drawing Sheets

(a)

(b)

US 10,241,065 B2

ANALYSIS METHOD FOR POLYOLEFIN BRANCHES AND SYSTEM USING SAME

CROSS REFERENCE TO RELATED APPLICATION

This application is a National Stage Application of International Application No. PCT/KR2014/009756, filed Oct. 16, 2014, and claims priority to and the benefit of Korean Patent Application No. 10-2013-0124625, filed Oct. 18, 2013, the contents of which are incorporated by reference in their entirety for all purposes as if fully set forth below.

TECHNICAL FIELD

The present invention relates to a method of analyzing polyolefin branches and a system using the same.

BACKGROUND ART

The branch concentrations (ratios of branches) of polyolefin, including polyethylene and the like, are regarded as the main factor that affects the properties of products including melting, crystallinity, etc. Conventional methods of analyzing the branch concentrations are problematic because the testing time is long, whereby the type of sample that can be tested is limited and the feedback of analysis results is inevitably late. Hence, analysis methods are required to be improved in terms of shortening the testing time and increasing the sample preparation efficiency.

Conventionally useful in analyzing the branch concentrations of polyolefin, carbon NMR (Nuclear Magnetic Resonance) undesirably requires a measurement time of about 12 hr or longer. For example, there are provided analysis methods including measurement of the branch concentrations and qualitative and quantitative analysis of comonomers through 13C-NMR, mentioned in a paper by Professor Randall (Carbon-13 NMR of ethylene-1-olefin copolymers: Extension to the short-chain branch distribution in a low-density polyethylene, Journal of Polymer Science: Polymer Physics Edition Volume 11, pages 275-287, February 1973). However, such methods are disadvantageous because of the long testing time and doubtful accuracy of values upon measuring short-chain branching using calibration curves, such as NIR, GPC, etc. In this regard, Korean Patent Application Publication No. 2007-0088724 discloses a method of analyzing the structure of a compound using H-NMR and 13C-NMR, but methods of analyzing the ratios of polyolefin branches have not yet been introduced.

Accordingly, there is a need for novel analysis methods that are able to drastically reduce the measurement time and are also able to analyze low-concentration samples.

DISCLOSURE

Technical Problem

The present invention has been made keeping in mind the above problems encountered in the related art, and an object of the present invention is to provide a novel method of analyzing the ratios of branches of polyolefin, which may remarkably decrease the measurement time and may be used to analyze low-concentration samples, unlike conventional analysis methods.

Technical Solution

In order to accomplish the above objects, the present invention provides a method of analyzing polyolefin branches, comprising: a) obtaining a spectrum for a sample including polyolefin having a plurality of branches using an NMR spectrometer and a pulse program, wherein the peaks of the branches are separated from each other in the spectrum; and b) calculating the proportion of each of the branches using the separated peaks.

In addition, the present invention provides a system for analyzing polyolefin branches, comprising: a) a peak separation module for obtaining a spectrum for a sample including polyolefin having a plurality of branches using an NMR spectrometer and a pulse program, wherein the peaks of the branches are separated from each other in the spectrum; and b) a calculation module for calculating the proportion of each of the branches using the separated peaks.

Advantageous Effects

According to the present invention, a method of analyzing polyolefin branches can remarkably decrease the measurement time, and can analyze low-concentration samples, unlike conventional analysis methods, thereby enabling the analysis of the ratios of branches of polyolefin.

BEST MODE

Hereinafter, a detailed description will be given of the present invention.

According to the present invention, a method of analyzing polyolefin branches comprises: a) obtaining a spectrum for a sample including polyolefin having a plurality of branches using an NMR spectrometer and a pulse program, wherein the peaks of the branches are separated from each other in the spectrum; and b) calculating the proportion of each of the branches using the separated peaks.

In a) of the method of analyzing the polyolefin branches according to the present invention, the spectrum for the sample including polyolefin having a plurality of branches is obtained using an NMR spectrometer, and then the peaks of the branches in the obtained spectrum are separated from each other.

In the present invention, the analyte is a sample including polyolefin, and polyolefin may be any one of polyethylene, polypropylene, polybutene, and low-density polyethylene (LDPE). Preferably useful is polyethylene.

The polyolefin may contain a plurality of branches. As used herein, the term 'branch' refers to an additional chain, instead of hydrogen, which may be connected to carbon of the main chain of polyolefin. For example, when PE has many branches, the density thereof is decreased, resulting in low-density polyethylene (LDPE). On the other hand, when PE has few branches, the density thereof is increased, resulting in high-density polyethylene (HDPE). Typically, linear polyolefin is stronger than non-linear polyolefin, but non-linear polyolefin is inexpensive and is easy to mold.

Figure 1:
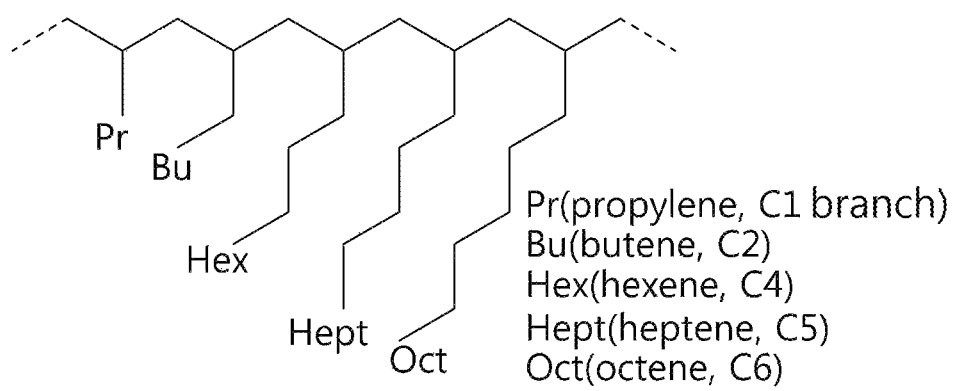
FIG. 1 illustrates the nomenclature of polyolefin branches according to the present invention.

As illustrated in FIG. 1, the branches of polyolefin may include a C1 branch comprising a propylene branch having a main chain, a C2 branch comprising a butene branch having a main chain, a C3 branch comprising a pentene branch having a main chain, a C4 branch comprising a hexene branch having a main chain, a C5 branch comprising a heptene branch having a main chain, and a C6 branch comprising an octene branch having a main chain. The branches of polyethylene are classified into short-chain branches (SCBs) and long-chain branches (LCBs). Generally, a C6 or higher branch prepared from a 1-octene comonomer is defined as LCB. In the present invention, polyolefin may contain both SCB and LCB. Preferably, polyolefin has two or more of C1 to C6 branches defined as above, such as propylene, butene, pentene, hexene, heptene and octene.

In the method of analyzing polyolefin branches according to the present invention, the sample including polyolefin is processed using an NMR spectrometer and a pulse program, thus obtaining a spectrum in which the peaks of the branches thereof are separated from each other. The NMR spectrometer and the pulse program may be selectively used depending on the type of branch of the polyolefin analyte. The NMR spectrometer is not particularly limited so long as it is a $^1$H-NMR spectrometer, and preferably useful is a Bruker AVANCE III HD 700 MHz NMR spectrometer (700 mhz for proton and 176 MHz for carbon) provided with a Bruker BBO probehead (w/z-gradient) and Gradient unit [50 G/cm]. The pulse program may include a homo-decoupling pulse program or a pulse program using a proton-carbon hetero correlation 2D method, and may specifically include zghd.2 or zghd.3 contained in s/w Topspin v3.2 made by Bruker, a $^1$H-$^{13}$C HMQC pulse program or a $^1$H-$^{13}$C HSQC pulse program. The measurement time when using a homo-decoupling pulse program is about 2 to 5 min, and the measurement time when using a pulse program through a proton-carbon hetero correlation 2D method is about 10 to 30 min.

When the polyolefin analyte has two or more of hexene, heptene and octene branches, the coupling spectrum portion of the branches is subjected to homo-decoupling using an NMR spectrometer and a pulse program, thus obtaining a spectrum in which the peaks of the branches are separated from each other. When there appears a coupling phenomenon where hexene, heptene, and octene branch peaks are coupled in the obtained spectrum, the coupling is removed, that is, homo-decoupling is carried out, thereby separating the coupled peaks from each other.

Figure 2:
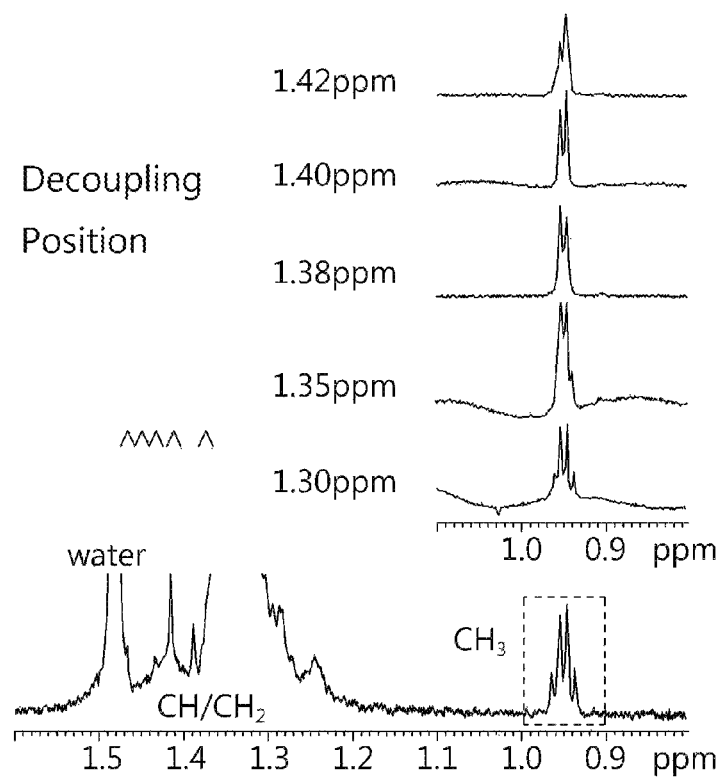
FIGS. 2(a) and 2(b) illustrates the separation of the branches in an NMR spectrum in Example 1 according to the present invention.
Figure 2:
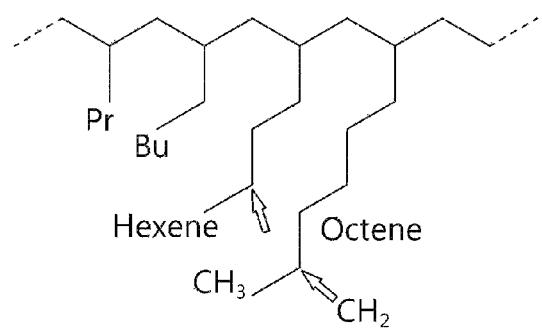

The homo-decoupling is specified below. As illustrated in FIG. 2(b), in polyethylene, having hexene and octene, the methyl peaks of hexene and octene show a triple coupling pattern, due to the methylene (CH2) peak at position 2 directly next thereto. When the decoupling position of the peaks thus coupled is changed, the methyl peaks of hexene and octene may be represented as two separated singlets in a specific region. Through the decoupling in which the coupling pattern of the methyl peaks is simplified into a singlet from a triplet, individual integral ratios of the monomers are determined, and the methyl regions of hexene and octene at 0.96 ppm in, for example, 1H-NMR are divided by the individual integral ratios, thereby determining molar ratios.

Hence, it is important to determine optimal values including the decoupling position and the decoupling width of the proton at position 2 of each monomer that is to be homo-decoupled. In the present invention, the homo-decoupling pulse program may include zghd.2 or zghd.3 contained in s/w Topspin v3.2 made by Bruker.

When the polyolefin analyte has propylene and butene branches, a 2D spectrum is obtained through a proton-carbon hetero correlation 2D method using a $^1$H-$^{13}$C HSQC pulse program or a $^1$H-$^{13}$C HMQC pulse program. More specifically, for polyethylene containing propylene (C1) and butene (C2), the methyl peaks of propylene (C1) and butene (C2) branches in the obtained spectrum are observed to be a doublet and a triplet, respectively, at almost the same position, and thus, even when homo-decoupling is carried out, two singlet methyl peaks cannot appear. Particularly, since the proton decoupling position (O2P) directly next to the methyl to be decoupled is spaced apart therefrom by about 0.1 ppm, even when the region decoupling pulse program is used, the decoupling efficiency may be remarkably decreased. However, as the carbon peak may be separated using a proton-carbon hetero correlation 2D method, the peaks of propylene (C1) and butene (C2) are separated from each other on the basis of the carbon peak, which will be described in the following example.

In the present invention, when the polyolefin analyte has two or more of propylene, butene, hexene, heptene and octene branches, that is, when it is a low-density linear polymer such as LDPE, the spectrum thereof is obtained using an NMR spectrometer, after which the peaks of the branches in the obtained spectrum may be separated from each other using a pulse program. As such, the peaks of hexene, heptene and octene branches are separated through homo-decoupling, and the peaks of propylene and butene branches may be separated through a proton-carbon hetero correlation 2D method.

In b) of the method of analyzing the polyolefin branches according to the present invention, the proportion of each of the branches is calculated using the separated peaks.

To calculate the proportion of each of the branches, the separated peaks are integrated using a homo-decoupling method or a proton-carbon hetero correlation 2D method, thus determining individual integral values of the branches. The proportion of each of the branches indicates the number of each branch relative to the total number of all branches contained in polyolefin, and preferably, the number of each branch per 1000 carbons, which are the total number of carbons of polyethylene, is calculated.

The number of each branch per 1000 carbons of polyolefin may be calculated using the following Equation 1.

$$\text{Number of branch } A \text{ per 1000 carbons} = [\text{molar ratio (branch } A) \times 1000]/[\text{molar ratio(polyolefin)} \times l_{PO} + \Sigma(\text{molar ratio(branch } k) \times l_k)] \quad \text{[Equation 1]}$$

(wherein branch k is each branch of polyolefin, $l_k$ is the number of carbons of the branch k monomer, and $l_{PO}$ is the number of carbons of the main-chain monomer of polyolefin.)

For example, in polyethylene, having branch A and branch B, the ratios of integral values of branch A and branch B are determined as follows: the integral value of branch A and the integral value of branch B are determined to be a and b (wherein when a>b, a=1, and when a<b, b=1), and the integral ratios of branch A and branch B are determined to be $R_A=a/(a+b)$ and $R_B=b/(a+b)$.

Furthermore, the compositions (molar ratios) of main-chain ethylene, branch A and branch B are determined using $R_A$ and $R_B$ values, based on the following Equation 2.

Main-chain Ethylene to Branch $A$ to Branch $B$=[integral value of CH and CH2 regions−(($M\times R_A$/3))$\times k_a$−(($M\times R_B$/3))$\times k_b$]/4:[($M\times R_A$)/3)]:[($M\times R_B$)/3)] [Equation 2]

(wherein M is the integral value of methyl region of branch A and branch B, $k_a$ is the number of protons of branch a other than $CH_3$, and $k_b$ is the number of protons of branch b other than $CH_3$.)

The molar ratios determined using Equation 2 are substituted into the following Equation 3, thus determining the numbers of branches A and B per 1000 carbons of polyethylene.

Number of branch $A$ per 1000 carbons=[molar ratio (branch $A$)×1000]/[molar ratio(ethylene)×2+ molar ratio(branch $A$)×$l_a$+molar ratio(branch $B$)×$l_b$] [Equation 3]

(wherein $l_a$ is the number of carbons of branch A, and $l_b$ is the number of carbons of branch B.)

The number of each branch per 1000 carbons may be determined from the values obtained by Equation 1, whereby the proportion of each of the branches is calculated.

For example, the number of 1-hexene branches per 1000 carbons in EHOR, having ethylene, hexene and octene, may be determined using the following Equation 4.

Number of 1-hexene per 1000 carbons=[molar ratio (1-hexene)×1000]/[molar ratio(ethylene)×2+ molar ratio(1-hexene)×6+molar ratio(1-octene)× 8] [Equation 4]

When the 2D spectrum is obtained using a $^1H$-$^{13}C$ HMQC pulse program or $^1H$-$^{13}C$ HSQC pulse program, the separated peaks of the branches are integrated through 2D peak integration. The number of carbons of each branch may be determined from the integral values, whereby the proportion of each of the branches may be calculated. The numbers of the branches may be calculated using Equations 1 to 4.

Upon using a $^1H$-$^{13}C$ HMQC pulse program or a $^1H$-$^{13}C$ HSQC pulse program, the methyl peaks of propylene (C1) and butene (C2) are separated, after which the contents thereof may be measured through 2D peak integration. Since 2D peaks are available under the condition that quantitative reliability is ensured, a $^1H$-$^{13}C$ HMQC NMR spectrometer in magnitude mode having high sensitivity is preferably used, rather than a $^1H$-$^{13}C$ HSQC spectrometer in phase-sensitive mode with high resolution.

According to the present invention, a system for analyzing polyolefin branches comprises: a) a peak separation module for obtaining a spectrum for a sample including polyolefin having a plurality of branches using an NMR spectrometer and a pulse program, wherein the peaks of the branches are separated from each other in the spectrum; and b) a calculation module for calculating the proportion of each of the branches using the separated peaks.

In the analysis of polyolefin branches according to the present invention, the polyolefin may be any one selected from among polyethylene, polypropylene, polybutene and LDPE, and the polyolefin may contain two or more of propylene, butene, pentene, hexene, heptene and octene branches.

In the system for analyzing the polyolefin branches according to the present invention, when polyolefin having the branches contains two or more of hexene, heptene and octene branches, the peak separation module of a) operates in a manner such that the coupling spectrum portion of the branches is subjected to homo-decoupling using a pulse program, thus separating the peaks of the branches from each other.

In the system for analyzing the polyolefin branches according to the present invention, when the polyolefin having the branches contains propylene and butene branches, the peak separation module of a) operates in a manner such that a 2D spectrum is obtained using a proton-carbon hetero correlation 2D method through a pulse program, and then the peaks of the branches may be separated from each other. The above pulse program may be a $^1H$-$^{13}C$ HMQC pulse program or a $^1H$-$^{13}C$ HSQC pulse program. As such, the calculation module of b) operates in a manner such that the proportion of each of the branches is calculated by integrating the separated peaks of the branches to obtain individual integral values thereof, determining individual integral ratios of the branches from the integral values, and determining individual molar ratios of the branches from the integral ratios.

In the system for analyzing the polyolefin branches according to the present invention, the proportion of each of the branches in the calculation module of b) indicates the number of each branch per 1000 carbons of polyolefin.

In the system for analyzing the polyolefin branches according to the present invention, the number of each branch per 1000 carbons in the calculation module of b) may be calculated using the following Equation 1.

Number of branch $A$ per 1000 carbons=[molar ratio (branch $A$)×1000]/[molar ratio(polyolefin)×$l_{PO}$+ Σ(molar ratio(branch $k$)×$l_k$)] [Equation 1]

(wherein branch k is each branch of polyolefin, $l_k$ is the number of carbons of the branch k monomer, and $l_{PO}$ is the number of carbons of the main-chain monomer of polyolefin.)

As used herein, the term 'module' refers to a single unit for processing a specific function or operation, which may be embodied through hardware, software, or a combination of hardware and software.

Mode for Invention

A better understanding of the present invention may be obtained through the following examples which are set forth to illustrate, but are not to be construed to limit the present invention. The scope of the present invention is recited in the claims, and also contains all modifications within the ranges and meanings equivalent to the claims.

EXAMPLES

Example 1: Separation of Methyl Peaks of Hexene and Octene of EHOR

Polyethylene (EHOR, made by BASELL) containing 1-hexene and 1-octene was dissolved in a TCE-$d_2$ solvent at 100° C., thus preparing a sample having a concentration of 10 mg/mL, which was then measured for 2 min under the following 1H-NMR testing conditions:

NS: 16, D1: 3 sec, P1: ~30° Pulse width, Pulse program: zg, Temperature: 100° C.

Thereafter, the following optimal decoupling center was determined using zghd.3 contained in s/w Topspin v3.2 made by Bruker, as a homo-decoupling pulse program.

Specifically, the peak of methylene (CH2, the arrow portion of FIG. 2(b)), which is coupled with methyl of 1-hexene and 1-octene and is located at position 2 directly next thereto, was decoupled, whereby the coupling pattern of the methyl peak was simplified into a singlet from a triplet.

The optimal position of the decoupling center was searched in the range from 1.30 ppm to 1.42 ppm, and was thus determined to be 1.38 to 1.40 ppm. More specifically, when the decoupling center was 1.38 ppm and 1.39 ppm, there was almost no difference in the integral ratios between hexene and octene. However, when the decoupling center was 1.40 ppm, there was an integral ratio difference of about 10% therebetween. Taking into consideration the peak shape, the decoupling center of EHOR was set to 1.39 ppm.

Figure 3:
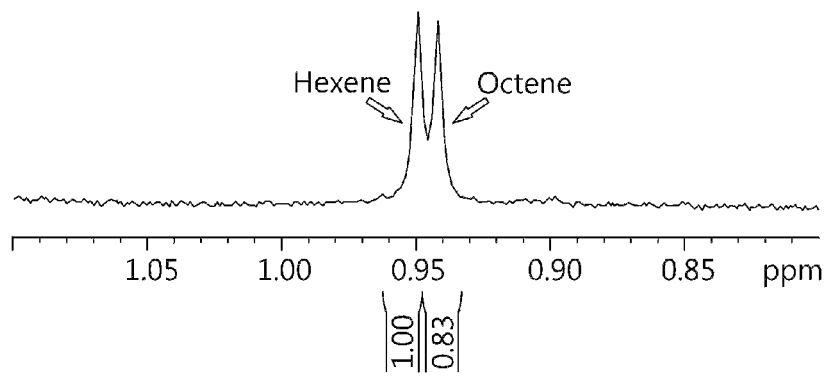
FIG. 3 illustrates the separation of the hexene and octene branches in an NMR spectrum in Example 1 according to the present invention.

Thereafter, the integral ratios of 1-hexene and 1-octene were determined as illustrated in FIG. 3 under the conditions of the decoupling center of 1.39 ppm, PLW 24=26.4 dB, P31=5 msec, D31=0.5 msec, and cpdprg2=hd, using a pulse program.

The integral values of hexene and octene were 1.00 and 0.83, respectively, and the integral ratios thereof were $R_{Hex}=1.00/(1.00+0.83)$ and $R_{Oct}=0.83/(1.00+0.83)$.

Figure 4:
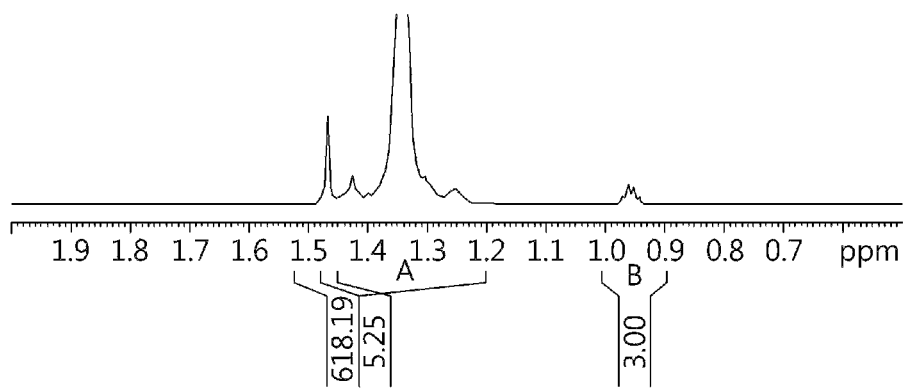
FIG. 4 illustrates the NMR spectrum of the sample of Example 1 according to the present invention.

Thereafter, the $^1$H-NMR peaks of the sample were determined as shown in FIG. 4, and the molar ratios of ethylene, 1-hexene and 1-octene were calculated below using individual integral values of the corresponding regions.

Ethylene(molar ratio) to 1-hexene(molar ratio) to
1-octene(molar ratio)=$[A-((B \times R_{Hex})/3) \times 9-(B \times R_{Oct}) \times 13]/4 : (B \times R_{Hex})/3 : (B \times R_{Oct})/3$ Using the individual molar ratios thus determined, the number of 1-hexene branches was calculated as follows.

Number of 1-hexene branches=[molar ratio(1-hexene)×1000]/[molar ratio (ethylene)×2+molar ratio(1-hexene)×6+molar ratio(1-octene)×8]

Number of 1-octene branches=[molar ratio(1-octene)×1000]/[molar ratio (ethylene)×2+molar ratio(1-hexene)×6+molar ratio(1-octene)×8]

The molar ratio, wt % ratio, number of 1-hexene branches per 1000 carbons, and number of 1-hexene branches per 1000 carbons are shown in Table 1 below.

TABLE 1

| Molar ratio | | | Mass % ratio | | | 1-Hexene/ | 1-Octene/ |
|---|---|---|---|---|---|---|---|
| Ethylene | 1-hexene | 1-octene | Ethylene | 1-hexene | 1-octene | 1000C | 1000C |
| 150.5 | 0.6 | 0.5 | 97.8 | 1.1 | 1.2 | 1.8 | 1.5 |

Example 2: Separation of Methyl Peaks of Propylene and Butene of EHBPR

Polyethylene (EHBPR, made by DNP) containing propylene and butene was dissolved in a TCE-d$_2$ solvent at 100° C., thus preparing a sample having a concentration of 10 mg/mL, which was then measured for 2 min under the following 1H-NMR testing conditions:

NS: 16, D1: 3 sec, P1: ~30° Pulse width, Pulse program: zg, Temperature: 100° C.

Thereafter, the sample was analyzed using hsqcedetgp (HSQC, FnMODE=echo-antiecho) and hmqcgpqf (HMQC, FnMODE=QF) contained in s/w Topspin v3.2 made by Bruker, as proton-carbon hetero correlation 2D pulse programs under the following parameters:

cnst2 [J(XH)=145 Hz], ns=4, d1=1.5 sec, TD=1K×128.

Figure 5:
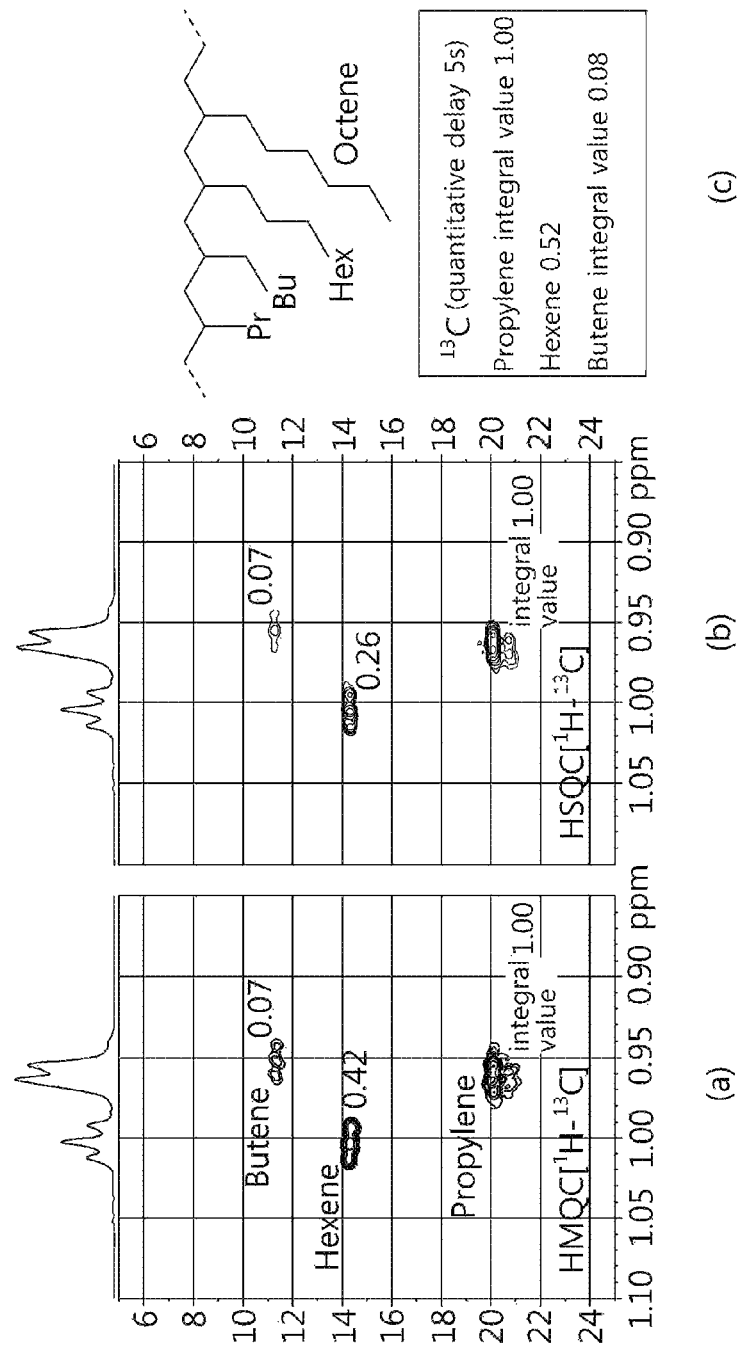
FIGS. 5(a) through 5(c) illustrates the separation of the branches in an NMR spectrum in Example 2 according to the present invention.

The results using hsqcedetgp (HSQC, Phase sensitive & CHn editing mode, FnMODE=echo-antiecho) and hmqcgpqf (HMQC, Magnitude mode, FnMODE=QF) as the 2D pulse programs are shown in FIG. 5(a). Assuming that the integral value of methyl peak of each monomer in $^{13}$C-NMR is the true value, when such integral values are compared with the 2D peaks of HSQC and HMQC, the integral values of metal peaks of butene and propylene at HSQC and HMQC were different less than about 10%. Also, the integral values of the spectrum of polyethylene (EHBPR) having propylene and butene measured using a $^{13}$C-NMR spectrometer are shown in FIG. 5(c). When compared with the 2D peaks of FIGS. 5(a) and 5(b), the values were very similar to each other.

The integral values of propylene and butene determined in FIG. 5(a) were 1.00 and 0.07, respectively and the integral ratios thereof were $R_{Pr}=1.00/(1.00+0.07)$ and $R_{Bu}=0.07/(1.00+0.07)$.

Figure 6:
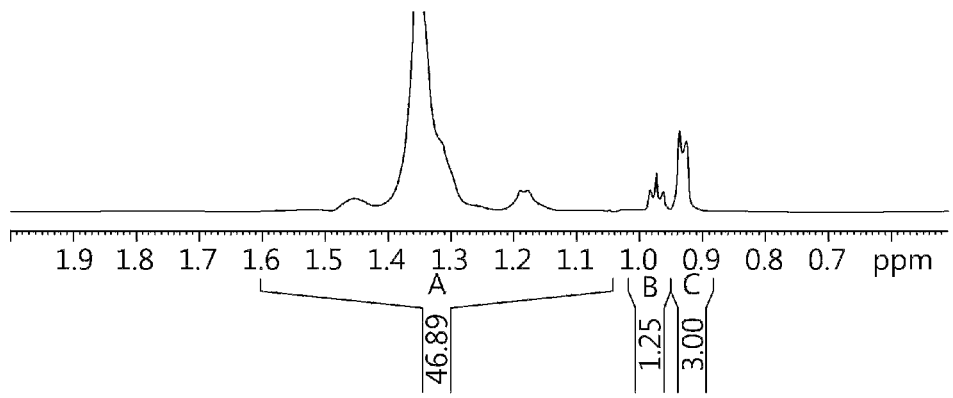
FIG. 6 illustrates the NMR spectrum of the sample of Example 2 according to the present invention.

The $^1$H-NMR peaks of the sample were determined as illustrated in FIG. 6, and the molar ratios of ethylene, 1-hexene, 1-butene and 1-propylene were calculated below using individual integral values of the corresponding regions.

Ethylene(molar ratio) to 1-hexene(molar ratio) to
1-butene(molar ratio) to 1-propylene=$[A-(B/3) \times 9-((C \times R_{Bu})/3) \times 5-((C \times R_{Pr})/3) \times 3]/4 : B/3 : (C \times R_{Bu})/3 : (C \times R_{Pr})/3$ Using the individual molar ratios thus determined, the number of 1-hexene branches was calculated as follows.

Number of 1-hexene branches=[molar ratio(1-hexene)×1000]/[molar ratio (ethylene)×2+molar ratio(1-hexene)×6+molar ratio(1-butene)×4+molar ratio(1-propylene)×3]

Number of 1-butene branches=[molar ratio(1-butene)×1000]/[molar ratio (ethylene)×2+molar ratio(1-hexene)×6+molar ratio(1-butene)×4+molar ratio(1-propylene)×3]

Number of 1-propylene branches=[molar ratio(1-propylene)×1000]/[molar ratio(ethylene)×2+molar ratio(1-hexene)×6+molar ratio(1-butene)×4+molar ratio (1-propylene)×3]

The molar ratio, wt % ratio, number of 1-hexene branches per 1000 carbons, number of 1-butene branches per 1000 carbons and number of 1-propylene branches per 1000 carbons are shown in Table 2 below.

TABLE 2

| Molar ratio | | | | Wt % ratio | | | | (1-Hexene)/ 1000C | (1-Butene)/ 1000C | (1-Propylene)/ 1000C |
|---|---|---|---|---|---|---|---|---|---|---|
| Et | Hex | Bu | Pr | Et | Hex | Bu | Pr | | | |
| 100.0 | 4.2 | 0.7 | 9.3 | 78.2 | 9.8 | 1.0 | 11.0 | 16.3 | 2.6 | 36.5 |

Example 3: Separation of Methyl Peaks of Hexene, Heptene and Octene of LDPE

For LDPE (low-density polyethylene, made by LG Chemical) containing propylene, butene, hexene, heptene and octene branches, two methods were used together in such a way that the ratios of methyl peaks of hexene, heptene, and octene were determined using the method of Example 1, and the ratios of methyl peaks of propylene and butane were determined using the method of Example 2.

For homo-decoupling of Example 1, zghd.3 [decoupling center=1.40 ppm, PLW24=26.4 dB, CPDPRG2=hd, P31=variable (1~5 msec), D31=0.5 ms] was used, and proton-carbon hetero correlation 2D of Example 2 was performed using hmqcgpqf [cnst2=145 Hz, ns=4, d1=1.5 sec, TD=1K×128].

Figure 7:
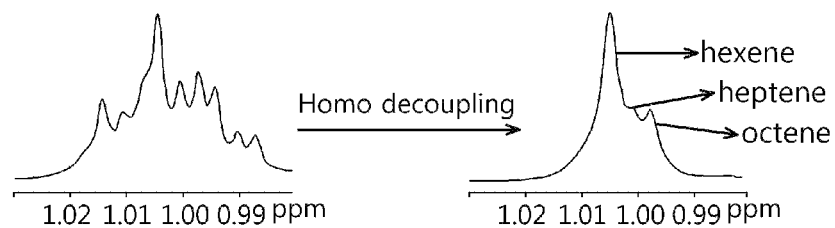
FIG. 7 illustrates the separation of the branches in an NMR spectrum in Example 3 according to the present invention.

Hexene (C4), heptene (C5), and octene (C6) underwent homo-decoupling, thus separating the individual methyl peaks thereof, as shown in FIG. 7.

Compared to Example 1, heptene was added, and thus a relatively low resolution was exhibited, but the branches were separated to the extent that the ratios of individual methyl peaks could be sufficiently determined through integration.

Figure 8:
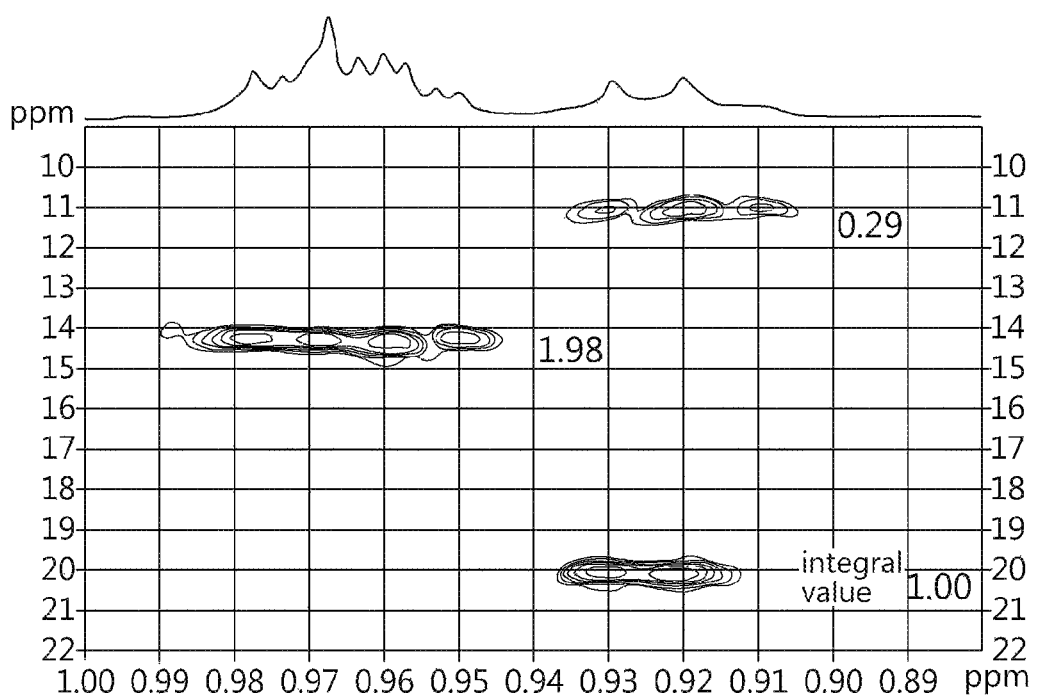
FIG. 8 illustrates the separation of the branches using a two-dimensional (2D) spectrum in Example 3 according to the present invention.

Propylene (C1) and butene (C2) underwent proton-carbon hetero correlation 2D, thus separating the individual methyl peaks thereof, as shown in FIG. 8.

Thereby, the compositions (wt %) of the branches of LDPE and the numbers of branches per 1000 carbons are given in Table 3 below.

TABLE 3

| Wt % ratio | | | | | | X/1000C | | | | |
|---|---|---|---|---|---|---|---|---|---|---|
| Et | Pr | Bu | Hex | Hept | Oc | Pr | Bu | Hex | Hept | Oc |
| 75.5 | 0.8 | 0.2 | 1.3 | 0.5 | 0.4 | 4.6 | 1.3 | 7.8 | 2.9 | 2.6 |

The numbers of branches per 1000 carbons analyzed using $^{13}$C-NMR were compared with the numbers of branches per 1000 carbons analyzed using homo-decoupling and HMQC in Example 3. The results are shown in Table 4 below.

TABLE 4

| Analysis method | X/1000C | | | | |
|---|---|---|---|---|---|
| | Pr | Bu | Hex | Hept | Oc |
| Example 3 | 4.9 | 1.4 | 8.4 | 3.1 | 2.8 |
| $^{13}$C-NMR | 3.1 | 4.1 | 9.6 | 3.3 | 3.7 |

As is apparent from Table 4, there is a slight difference therebetween, but the contents of the branches analyzed using homo-decoupling and HMQC were similar to those analyzed using $^{13}$C-NMR.

The invention claimed is:

1. A method of analyzing polyolefin branches, comprising:
   a) obtaining a spectrum for a sample including polyolefin having a plurality of branches using a nuclear magnetic resonance (NMR) spectrometer and a pulse program, wherein peaks of the branches are separated from each other in the spectrum; and
   b) calculating a proportion of each of the branches relative to the total number of all branches contained in polyolefin using the separated peaks,
   wherein when the polyolefin has two or more of C4, C5, and C6 branches respectively from hexene, heptene and octene comonomers, and when the two or more branches are different from each other, a coupling spectrum portion of the branches is subjected to homo-decoupling using a homo-decoupling pulse program in step a), so that peaks of the branches are separated from each other,
   wherein when the polyolefin has C1 and C2 branches respectively from propylene and butene comonomers, a two-dimensional (2D) spectrum is obtained through a 2D $^1$H-$^{13}$C heteronuclear correlation method using a pulse program in step a), and then peaks of the branches are separated from each other.

2. The method of claim 1, wherein the polyolefin is any one of polyethylene, polypropylene, polybutene, and low-density polyethylene (LDPE).

3. The method of claim 1, wherein the pulse program is a $^1$H-$^{13}$C HMQC pulse program or a $^1$H-$^{13}$C HSQC pulse program.

4. The method of claim 1, wherein in b), the proportion of each of the branches is calculated by integrating the separated peaks of the branches to obtain individual integral values thereof, determining individual integral ratios of the branches from the integral values, and determining individual molar ratios of the branches from the integral ratios.

5. The method of claim 4, wherein in b), the proportion of each of the branches is a number of each branch per 1000 carbons contained in the polyolefin.

6. The method of claim 5, wherein in b), the number of each branch per 1000 carbons is calculated using Equation 1 below, Number of branch A per 1000 carbons=[molar ratio (branch A)×1000]/[molar ratio(main-chain monomer of polyolefin)×$l_{PO}$+Σ(molar ratio (branch k)×$l_k$)]  [Equation 1]

wherein branch k is each branch of polyolefin, $l_k$ is a number of carbons of a branch k monomer, and $l_{PO}$ is a number of carbons of a main-chain monomer of polyolefin.

7. A system for analyzing polyolefin branches, comprising:
   a) a peak separation module for obtaining a spectrum for a sample including polyolefin having a plurality of branches using an NMR spectrometer and a pulse program, wherein peaks of the branches are separated from each other in the spectrum; and b) a calculation module for calculating a proportion of each of the branches relative to the total number of all branches contained in polyolefin using the separated peaks, wherein when the polyolefin has two or more of C4, C5, and C6 branches respectively from hexene, heptene and octene comonomers, and when the two or more branches are different from each other, the peak separation module of a) operates in a manner such that a coupling spectrum portion of the branches is subjected to homo-decoupling using a homo-decoupling pulse program, such that separating peaks of the branches from each other, and wherein when the polyolefin has C1 and C2 branches respectively from propylene and butene comonomers, the peak separation module of a) operates in a manner such that a 2D spectrum is obtained through a 2D $^1$H-$^{13}$C heteronuclear correlation method using a pulse program, and then peaks of the branches are separated from each other.

8. The system of claim 7, wherein the polyolefin is any one of polyethylene, polypropylene, polybutene, and LDPE.

9. The system of claim 7, wherein the pulse program is a $^1$H-$^{13}$C HMQC pulse program or a $^1$H-$^{13}$C HSQC pulse program.

10. The system of claim 7, wherein the calculation module of b) operates in a manner such that the proportion of each of the branches is calculated by integrating the separated peaks of the branches to obtain individual integral values thereof, determining individual integral ratios of the branches from the integral values, and determining individual molar ratios of the branches from the integral ratios.

11. The system of claim 10, wherein in the calculation module of b), the proportion of each of the branches is a number of each branch per 1000 carbons contained in polyolefin.

12. The system of claim 11, wherein in the calculation module of b), the number of each branch per 1000 carbons is calculated using Equation 1 below, $$\text{Number of branch } A \text{ per 1000 carbons} = [\text{molar ratio (branch } A) \times 1000] / [\text{molar ratio(main-chain monomer of polyolefin)} \times l_{PO} + \Sigma(\text{molar ratio (branch } k) \times l_k)] \quad \text{[Equation 1]}$$

wherein branch k is each branch of polyolefin, $l_k$ is a number of carbons of a branch k monomer, and $l_{PO}$ is a number of carbons of a main-chain monomer of polyolefin.

* * * * *